(12) United States Patent
Muller

(10) Patent No.: US 11,298,532 B2
(45) Date of Patent: Apr. 12, 2022

(54) IMPLANTABLE DIRECT-CURRENT ELECTRODE ASSEMBLY

(71) Applicant: Berlin Heals Holding AG, Zug (CH)

(72) Inventor: Johannes Muller, Berlin (DE)

(*) Notice: Subject to any disclaimer, the term of this patent is extended or adjusted under 35 U.S.C. 154(b) by 725 days.

(21) Appl. No.: 15/749,427

(22) PCT Filed: Jul. 27, 2016

(86) PCT No.: PCT/EP2016/067923
§ 371 (c)(1),
(2) Date: Jan. 31, 2018

(87) PCT Pub. No.: WO2017/021255
PCT Pub. Date: Feb. 9, 2017

(65) Prior Publication Data
US 2020/0114145 A1  Apr. 16, 2020

(30) Foreign Application Priority Data

Jul. 31, 2015 (EP) .................................... 15179354
Aug. 27, 2015 (EP) .................................... 15182642

(51) Int. Cl.
*A61N 1/05* (2006.01)
*A61N 1/20* (2006.01)

(52) U.S. Cl.
CPC ......... *A61N 1/0563* (2013.01); *A61N 1/0597* (2013.01); *A61N 1/205* (2013.01); *A61N 1/0573* (2013.01)

(58) Field of Classification Search
CPC ........ A61N 1/3752; A61N 1/056–0573; A61N 1/0587–059; A61N 1/0597; A61N 1/20; A61N 1/205
See application file for complete search history.

(56) References Cited

U.S. PATENT DOCUMENTS

| 4,603,705 A * | 8/1986 | Speicher ................. A61N 1/056 607/122 |
| 5,649,971 A | 7/1997 | Fain et al. |
| 5,928,277 A * | 7/1999 | Laske .................. A61N 1/0563 607/122 |
| 6,587,718 B2 | 7/2003 | Talpade |
| (Continued) | | |

FOREIGN PATENT DOCUMENTS

| EP | 0559932 A1 | 9/1993 |
| EP | 1870131 A1 | 12/2007 |
| WO | 2006/106132 A1 | 10/2006 |

*Primary Examiner* — Michael W Kahelin
(74) *Attorney, Agent, or Firm* — Lombard & Geliebter LLP; Antonio Papageorgiou

(57) ABSTRACT

An implantable direct-current electrode assembly (20, 120) has two implantable electrodes (30; 40) and a control circuit (50), to which the first and the second electrodes (30; 40) are electrically connected. The control circuit (50) is designed to establish a potential difference between the two electrodes (30; 40), so that a direct current (55) can flow between the two electrodes (30; 40). One of the electrodes (30) is a coil electrode with a maximum length that is pre-determined by the distance between the tricuspid valve and the end of the right ventricle lying opposite the tricuspid valve and the pulmonary valve. The counter-electrode (40) can be a coil electrode for the coronary sinus, or a plate electrode that can be attached to the exterior of the left ventricle.

8 Claims, 4 Drawing Sheets

(56) References Cited

U.S. PATENT DOCUMENTS

| | | |
|---|---|---|
| 7,319,898 B2 | 1/2008 | Hess |
| 2008/0195161 A1* | 8/2008 | Sakuma ............... A61N 1/0587 607/3 |
| 2008/0195163 A1 | 8/2008 | Scharmer |

* cited by examiner

IMPLANTABLE DIRECT-CURRENT ELECTRODE ASSEMBLY

TECHNICAL FIELD

The invention relates to an implantable direct-current electrode assembly with two implantable electrodes and a control circuit, wherein the two electrodes are connected to the control circuit, wherein the control circuit is designed to establish a potential difference between the two electrodes, such that a direct current can flow between these electrodes.

PRIOR ART

An electrode assembly of this kind is known from WO 2006/106132, which discloses an electrode for treatment of organic tissue by means of direct current, wherein surface electrodes are provided in order to allow direct current of defined magnitude to flow through the largest possible tissue area of the myocardium via the surface electrodes.

The prior art also discloses implantable electrodes which are used as so-called coil electrodes for defibrillation of hearts with an arrhythmic beat. These electrodes are moreover used to emit electrical current impulses via their tip anchored in the heart tissue and/or via an electrode ring in the proximity of the electrode tip and/or to detect the ECG for controlling the implant (sensing function of the electrode). The prior art knows such electrodes particularly insofar as they are provided as cardiac pacemaker electrodes, as pulse-emitting electrodes or sensing electrodes. The housing of the implant is often used as counter-electrode (unipolar stimulation, unipolar sensing). It is advantageous here if the coil electrode is advanced endocardially into the right ventricle. Such coil electrodes are provided with a tip which can be anchored in the myocardium in order then to forward the current impulse via this tip, or via an electrode ring in the proximity of the tip, into the tissue connected thereto, with the aim of increasing the electrical excitation of the heart (increase in heart rate) and/or improving the electrical excitation of the heart (synchronization; CRT function) and/or detecting the ECG of the heart. It is also known from the prior art, as a counter-electrode to the coil electrode, to place a further electrode into the coronary sinus, i.e. the vein of the coronary system of the heart (bipolar stimulation). It is thus possible, also with such an electrode assembly, to electrically excite the heart with the aim of increasing the heart rate, synchronizing the electrical stimulus conduction in the heart and/or using bipolar sensing to control or regulate the implant. The advantage of a bipolar electrode configuration often lies in better sensing and/or stimulating behavior with lower energy consumption.

U.S. Pat. No. 7,319,898 B2 discloses a system comprising a defibrillator with a self-adapting defibrillator induction feature, in order to assess the efficacy of the defibrillator in detecting and terminating the fibrillation of a heart. A number of coil electrodes are arranged in the heart in order to achieve this function.

U.S. Pat. No. 6,587,718 B2 relates to an iontophoretic delivery of a therapeutic agent to heart tissue, wherein the therapeutic agent is introduced to a first side of the heart tissue. An electrode is arranged percutaneously on a second side of the heart tissue and is energized to induce migration of the therapeutic agent into the heart tissue.

Further prior art documents pertaining to the technical background are EP 1 870 131 A1 for a ventricular device preventing fibrillation, EP 0 559 932 A1 for an implantable assembly for effecting defibrillation of a heart using a planar electrode, and U.S. Pat. No. 5,649,971 A for a further device and method for inducing fibrillation.

DISCLOSURE OF THE INVENTION

Proceeding from this prior art, the object of the invention is to make available an electrode assembly for improving the effect of direct current in order to heal the diseased myocardium and in particular for increasing the safety of treatment.

According to the invention, the object is achieved with an electrode assembly having the features of claim 1. One electrode is a coil electrode with a maximum length that is predetermined by the distance between the tricuspid valve and the end of the right ventricle lying opposite the tricuspid valve and pulmonary valve, which means that coil electrodes of predefined length are provided in the implantable direct-current electrode assembly according to the invention, wherein the operating surgeon advantageously selects a coil electrode which as far as possible covers said distance. However, shorter electrodes can also be used, wherein the length of the ventricular coil electrode is defined by the one conductive metallic sheath surface or coil surface defining a sheath. For example, it has a length of 4 to 12 centimeters, in particular ca. 6 to 10 centimeters, and either 6 to 7 or 8 at 10° C.) and is designed such that, after passage through the right cardiac valve, to fill as far as possible the entire length of the right ventricle. In standard uses, the surface surrounding the electrode should a for example between 3 and 5, in particular 4 to 4.5 cm$^2$, and can be made of a palladium-iridium alloy.

Thus, compared to the known surface electrode assembly for the use of direct current, another electrode assembly is made available which in particular permits minimally invasive implantation of a device with which direct-current treatment of the heart is possible, which is intended to serve to heal the myocardium but which has no effect on the excitation or contraction of the heart (non-stimulating [subliminal] direct-current treatment of the heart).

It is therefore particularly advantageous that such direct-current treatment of the heart lasts for an average of a few months to a maximum of six months, and this period of time also corresponds to the battery operating time for such direct-current treatment. This battery operating time is of course greatly reduced by comparison with the battery operating time of cardiac pacemaker electrodes since, in contrast to the pulse systems there, a continuously flowing, low direct current places a load on the battery here. The aim is to permit treatment for a period of 6 months and upward, even up to one year. As per the definition of direct current, the device can be designated here as a direct-current electrode assembly for substantially constant non-pulsing direct current. That is to say, except for predetermined changes of the current strength, a current flowing constantly in one direction is provided for periods of time ranging from minutes to several hours, after which the current direction can be reversed in order to avoid the appearance of disruptive electrolysis products on the electrodes. The current strengths used preferably lie between 0.001 and 10 milliamperes. The current density lies, for example, between 0.01 microampere per square centimeter and 0.1 milliampere per square centimeter. The current density can advantageously be maintained in a range of 0.1 to 20 microamperes per square centimeter, preferably between 1 and 15 microamperes per square centimeter, by preference between 5 and 10 microamperes per square centimeter.

For this very reason, it is of interest that the treating physician can put the electrodes into place by a minimally invasive route. An advantage of the use of coil electrodes over surface electrodes is that the current can then no longer use the liquid film present on the myocardium as a path of lower electrical resistance (short-circuit current) for the current flow between the two electrodes. With two electrodes placed on the myocardium, there is the possibility that the current flows over such a conductive layer present on the surface with low electrical resistance and does not use the direct short path through the heart muscles with higher electrical resistance between the two surface electrodes.

An implantable direct-current electrode assembly has two implantable electrodes and a control circuit, wherein the first and the second electrode are electrically connected to the control circuit via preferably single-conductor, insulated lines, wherein the control circuit is designed to establish a potential difference between the two electrodes, such that a direct current can flow between the two electrodes, while one electrode is a coil electrode with a maximum length that is predetermined by the distance between the tricuspid valve and the end of the right ventricle lying opposite the tricuspid valve and pulmonary valve (tip of the right ventricle).

The other electrode can alternatively be a coil electrode for the coronary sinus, or a surface electrode for applying to the exterior of the left ventricle. A surface electrode has a conductive surface of not more than 40 $cm^2$, and the total surface area of the electrode should not exceed 90 times 60 mm. The surface electrode can in particular be a substantially rectangular to slightly trapezoid surface, i.e. a reduction of the width from for example 8 cm to less than 6 cm over a length of 6.5 to 8 cm, wherein on the larger side of the trapezium, after ca. ⅓ of the length, a V-shaped incision of below 3 to 4 cm is provided on both sides, such that two flexible flaps are formed on each side next to the central region. On the narrower trapezium side, a tab is provided for an electrical supply line that is to be applied, which supply line is brought up to and clipped onto this opening.

Advantageously, the first coil electrode is composed exclusively of one or more windings, such that there is no complicated structure there with sensors or with an implantable tip. The distal end of the first coil electrode is preferably blunt, in order to ensure that this electrode comes to lie only in the apex of the right ventricle, and the ventricle wall or the ventricle septum is not perforated. The coil electrodes according to the invention can therefore comprise a simple spiral and in particular require no sensing electrodes for feedback of the reaction of the heart. Moreover, they also advantageously do not comprise an anchorable tip provided with barbs. They are designed to come to lie loosely in the ventricle or in the coronary sinus.

Advantageously, the coil electrode to be inserted into the right ventricle has a larger diameter than in the case of known coil electrodes provided for defibrillation and/or pulse transmission for excitation with subsequent contraction, since the current from the electrode body lying on the ventricle wall of the right ventricle is transferred via blood and myocardial tissue to the counter-electrode and is not transmitted via the tip of the electrode into the myocardial tissue. The greater diameter and therefore the greater current-releasing surface permit a greater current, without exceeding a predetermined maximum current density that is reasonable for optimal therapy. They additionally have the advantage of passing current through a larger area of tissue of the myocardium.

In another illustrative embodiment, the electrode assembly comprises, in addition to the coil electrode provided for the right ventricle, a second electrode in the form of a surface electrode which is applied to the left part of the heart. Here, the advantage over the prior art is that the path of the electrical current through the myocardial tissue is guaranteed, since there is no current flowing off at the heart surface. On the other hand, a patch electrode of large surface area affords the advantage that the current issuing from the coil electrode widens out in a fan shape and flows through a large part of the myocardial tissue. This is entirely in keeping with direct-current treatment since, in contrast to the cardiac pacemaker, no impulses to support the heart activity need to be generated in order to stimulate the myocardium at a defined location, and instead a low current that is to be output over a long period of time is the aim of using the electrode assembly, which flows through the myocardial muscle has the effect that the diseased musculature is regenerated.

In the implantable direct-current electrode assembly, the electrical connection between the first and second electrodes and the control circuit can advantageously be designed as insulated, single-conductor lines.

In an advantageous embodiment of the coil electrode for the implantable direct-current electrode assembly, this is composed exclusively of one or more electrically conductive windings which are wound around an electrode core made of electrically insulating material and connected integrally to the insulating sheath of the supply line. The diameter of the windings can be 0.10 to 0.20, in particular 0.15 millimeter.

Advantageously, the distal end of the first coil electrode, and optionally that of the second coil electrode, is blunt and extends past the end of the winding(s), such that it can bear in an electrically insulating manner on the ventricle floor in the region of the apex of the ventricle.

In another embodiment, the distal end of the first coil electrode can be composed of a plurality of free ends which protrude from one another and which can be designated as barbs, and which extend past the end of the winding(s), such that these anchoring tips can be advanced into the muscle tissue and the trabecular network in order to ensure electrically insulated anchoring. The free ends taper to a point and/or can be hook-shaped. The current then issues substantially from the side face of the windings lying opposite the second electrode and flows through the blood-filled right ventricle and the interventricular septum to the counter-electrode of the left ventricle.

Here, the "end of the right ventricle" relates in other words to the apex of the right ventricle.

A separate electrically insulating anchor can be provided on the tip and anchoring tips can be arranged thereon. Advantageously, the anchor is a hollow cylinder and is connected passively, e.g. adhesively bonded, to the electrode reaching into it. The electrode can be guided in the anchor as far as an end cap inserted in the latter, which end cap can itself be a hollow cylinder in order to receive the tip of the electrode wire. A purpose of the end cap is then to cover the distal end of the conductor in an electrically insulating manner and mechanically, the latter in order to avoid engagement of an inserted mandrel into the anchor, through the latter and out of it.

Further embodiments are set forth in the dependent claims.

BRIEF DESCRIPTION OF THE DRAWINGS

Preferred embodiments of the invention are described below with reference to the drawings, which serve only for explanatory purposes and are not to be interpreted as limiting the invention. In the drawings.

DESCRIPTION OF PREFERRED EMBODIMENTS

Figure 1:
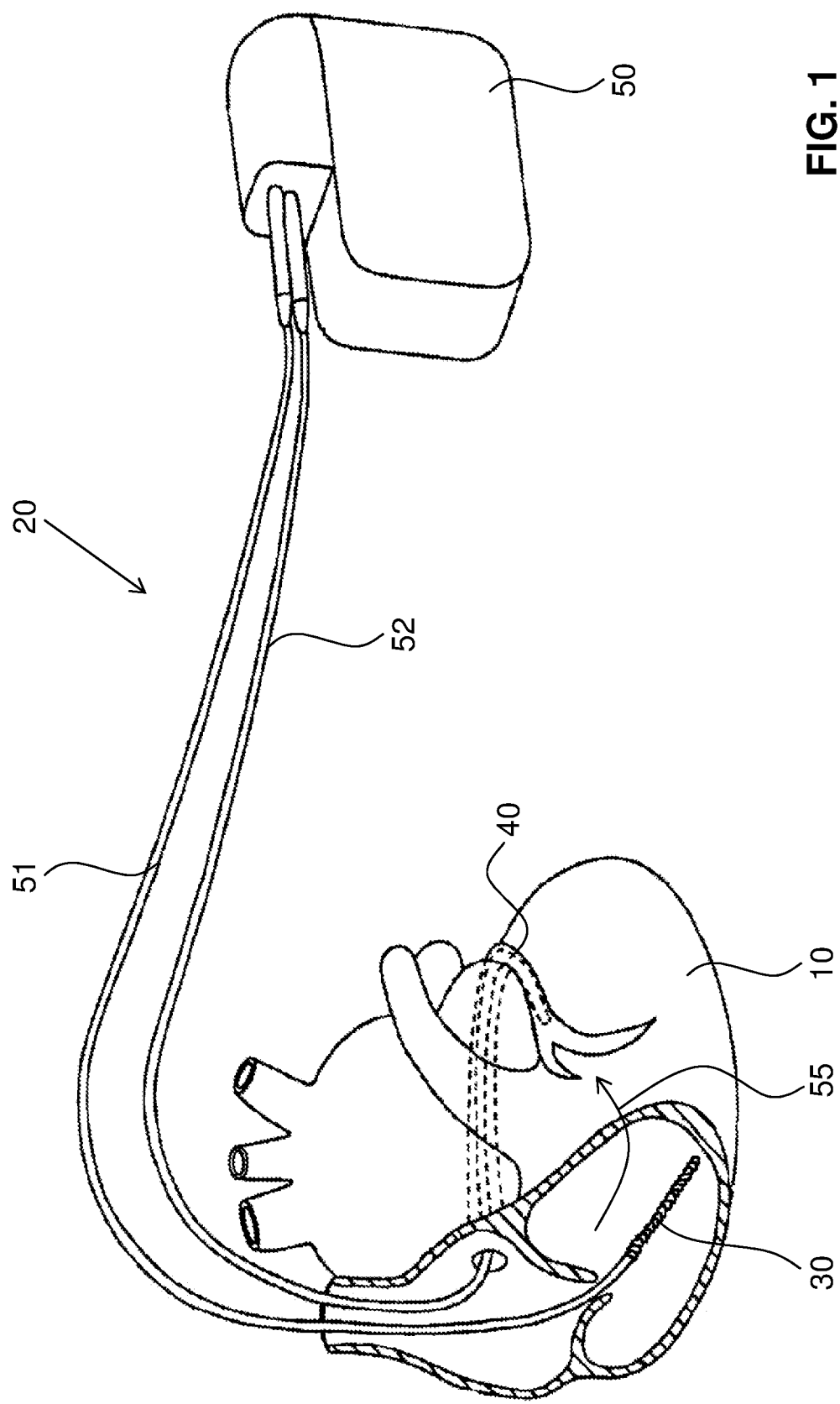
FIG. 1 shows a schematic representation of a heart with an electrode assembly according to a first illustrative embodiment of the invention.

FIG. 1 shows a schematic representation of a heart 10 with an electrode assembly 20 according to a first illustrative embodiment of the invention. The implantable direct-current electrode assembly 20 comprises two implantable electrodes 30 and 40 and a control circuit 50, usually arranged in a separate housing in which the battery for the power supply is likewise provided.

The two electrodes 30 and 40 are connected to the control circuit 50 via two single-conductor cables 51 and 52.

The control circuit 50 is designed to establish a potential difference between the two electrodes 30 and 40, such that a direct current can flow between these electrodes 30 and 40.

Figure 4:
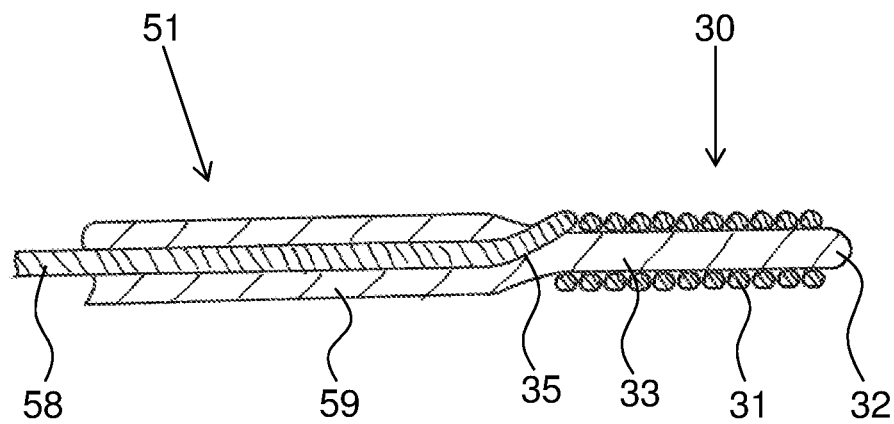
FIG. 4 shows a schematic representation of another coil electrode according to a further illustrative embodiment of the invention for use as a ventricular electrode as per FIG. 1 or FIG. 2.

One electrode 30 is a ventricular electrode, provided for positioning in the right ventricle, and is designed as a coil electrode. It is therefore designated below as a ventricular coil electrode 30. The length of the ventricular coil electrode 30, defined by the one conductive metallic sheath surface or coil surface defining a sheath, is ca. 8 to 10 centimeters and is designed to fill as far as possible the entire length of the right ventricle after passage through the right cardiac valve. Here, the ventricular coil electrode 30 is placed loosely into the right ventricle, but it can touch the wall of the right ventricle. An electrode as shown in FIG. 4, and as described below, can advantageously be used here.

Figure 2:
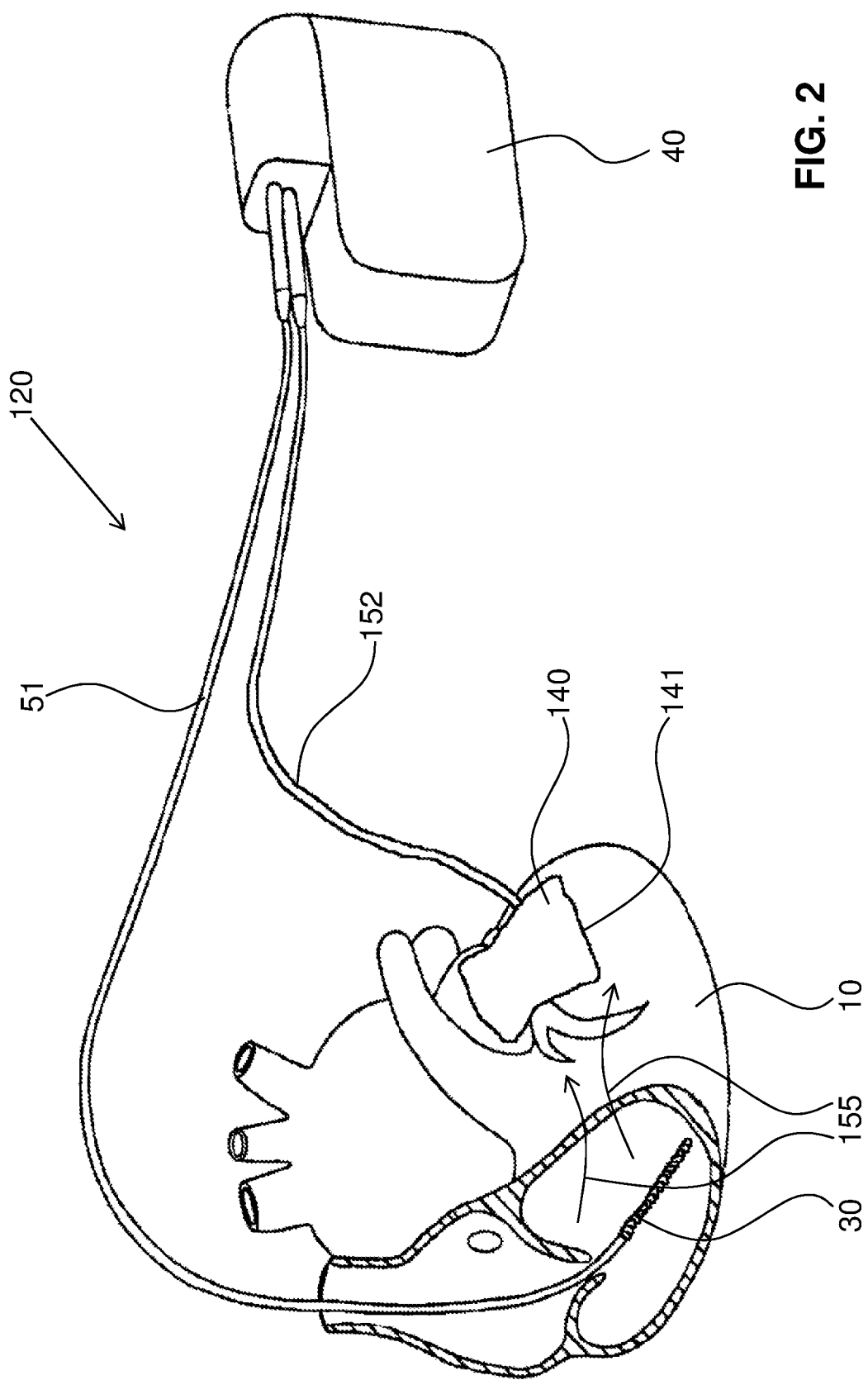
FIG. 2 shows a schematic representation of a heart with an electrode assembly according to a second illustrative embodiment of the invention.

From FIGS. 1 and 2, the electrode 30 seems to float freely in the right ventricle. However, this is only apparently the case, because the figures are schematic two-dimensional depictions. Generally, the electrode 30 will nestle on the wall of the ventricle; in the depiction in FIG. 2, this could be the posterior wall, which is not visible there. The electrode 30 is flexible in order to adopt these gentle curvatures, which amount to less than 30 degrees with respect to the longitudinal axis.

The other electrode 40 is a coronary sinus electrode, provided for positioning in the coronary sinus, and is likewise designed as a coil electrode. This coronary sinus coil electrode 40 has a smaller diameter than the ventricular coil electrode 30 since it is intended to be advanced far into the coronary sinus in order then to come to lie in the narrowing end region there. This electrode thus lies at a position substantially predefined by the vessel walls, which position the operating surgeon otherwise establishes by advancing it in the longitudinal direction.

When the two electrodes 30 and 40 are subjected to a potential difference by the control circuit 50 via the attachment wires or cables 51, 52 insulated from the environment, a direct current then flows according to the arrow 55 through the myocardium. In a manner predetermined by the control circuit, the electrode 30 can be the cathode for a predetermined time of between a few minutes and a few hours, whereby the direction of the current is predefined. The control circuit can then change the direction of the current after a correspondingly predetermined time, whereby the electrode 40 becomes the cathode. The current strength can also change, since the resistance between the two electrodes 30 and 40 is dependent on the direction of the current. In a further illustrative embodiment, the control device controls the current strength at a uniform predetermined value.

Figure 3:
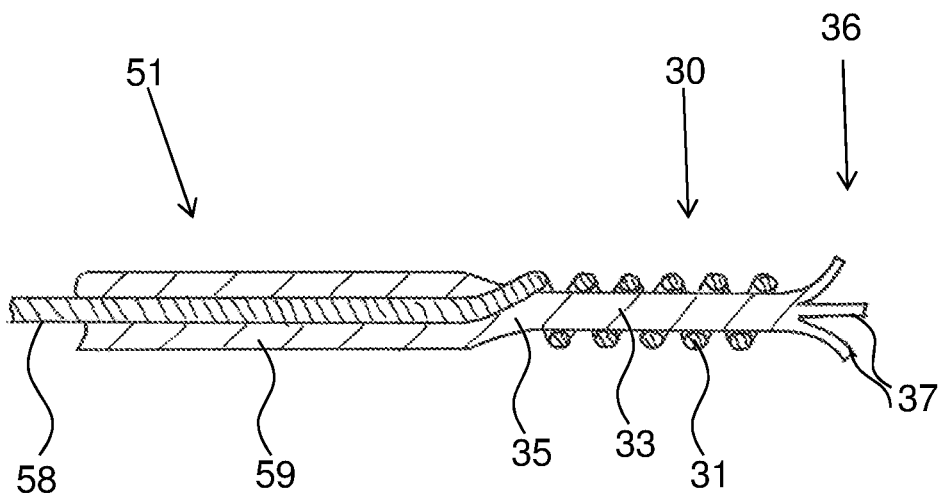
FIG. 3 shows a schematic representation of a coil electrode according to a further illustrative embodiment of the invention for use as a ventricular electrode as per FIG. 1 or FIG. 2.

Two embodiments of coil electrodes 30 for use in this assembly 20 are shown in greater detail in FIGS. 3 and 4. Although the electrodes in these figures always carry the reference sign 30, they are also usable, when scaled down, as electrodes 40, in particular the electrode according to FIG. 4.

FIG. 2 shows a schematic representation of a heart 10 with an electrode assembly 120 according to a second illustrative embodiment of the invention. The implantable direct-current electrode assembly 120 comprises two implantable electrodes 30 and 140 and also a control circuit 50.

Identical features are provided with identical reference signs, similar features with correspondingly similar reference signs.

The control circuit 50 can be designed in the same way as described in FIG. 1. The two electrodes 30 and 140 are also connected to the control circuit 50 via two single-conductor cables 51 and 52.

The control circuit 50 is also designed here to establish a potential difference between the two electrodes 30 and 140, such that a direct current can flow between these electrodes 30 and 140 for a predetermined time of several minutes, e.g. 5 minutes, to several hours, e.g. 3 hours. After this time period, the polarity of the voltage supply is reversed such that, over the course of time, no substantial residues can form on the electrodes and in the tissue in accordance with the electrochemical reactions. The direct current can a magnitude of between One electrode 30 is once again a ventricular electrode, provided for positioning in the right ventricle, and is designed as a coil electrode. It is therefore also designated here as a ventricular coil electrode 30. The length of the ventricular coil electrode 30, defined by the one conductive metallic sheath surface or coil surface defining a sheath, is ca. 6 to 9 centimeters and is designed to fill as far as possible the entire length of the right ventricle in the longitudinal axis after passage through the right cardiac valve. Here, the ventricular coil electrode 30 is placed loosely into the right ventricle, is passively anchored at the distal end and can bear on the wall of the ventricle or on the septum.

The other electrode 140 is a surface electrode, provided for positioning on the myocardium. It can be designed, for example, according to the teaching of US 2008/0195163 A1. This surface electrode 140 is applied to the left side of the myocardium, epicardially opposite the right ventricle.

When the two electrodes 30 and 140 are subjected to a potential difference by the control circuit 50 via the attachment wires or cables 51, 52 insulated from the environment, a direct current then flows according to the arrows 155 through the myocardium. This flow of current is symbolized here by two arrows, since the flow of current here fans out from a substantially longitudinally dimensional face of the substantially longitudinally oriented surface of the coil electrode 30 toward the surface electrode 140 and thus sweeps across a fan. Seen physically, the direct current flows through a prism; that is to say proceeding from an edge (of the prism) to its base on the patch electrode.

A prism is by definition a geometric body whose side edges are parallel and of equal length and which has a polygon as base. It arises from parallel displacement of a plane polygon along a straight line not lying in this plane and is therefore a special polyhedron. Here, the straight line is predefined by the longitudinal axis of the coil electrode 30, and the polygon is a triangle with the apex at the coil electrode 30 and with a base that corresponds to the width of the surface electrode 140. If these side edges 141 of the surface electrode 140 do not come to lie parallel to the orientation of the coil electrode, it is a rotated prism. In all cases, the two electrodes 30 and 140 define a not inconsiderable spatial body which guarantees that the direct current emitted by the control circuit 50 flows through a likewise not inconsiderable subregion of the left cardiac muscle and to a slightly lesser extent also of the right cardiac muscle. Describing the geometry of the body through which the current flows as a prism is an approximation, since it can be assumed from this that the electrode does not float freely but is instead passively fixed at its distal tip and then bears on the wall of the ventricle. The boundary lines of the body are then certainly not straight but curved, and the defined body is then obtained only approximately as a prism. Of importance, however, is the narrow "edge" on the one side formed by the coil electrode, and the "broad bottom face" on the other side which is formed by the patch electrode.

A coil electrode 30 for use in this assembly 120 is shown in greater detail in FIG. 3. FIG. 3 shows a schematic representation of a coil electrode for use as a ventricular electrode in an illustrative embodiment according to FIG. 1 or FIG. 2. This electrode 30 is formed by fewer elements than a conventional coil electrode.

The supply line 51 has a conductive single-conductor core 58, which is surrounded by an insulating sheath 59. The sheath 59 ends in a region before the electrode 30, that the long wound end 31 described in connection with FIGS. 1 and 2. The single-conductor core 58 emerges from the sheath 59 in the transition region 35.

The electrode tip core 33 has a smaller diameter than the sheath 59, advantageously in such a way that the overall diameter of the electrode 30, constructed from the winding and the electrode tip core 33, is still smaller than the sheath 59 or at most the same size as the latter.

The coil electrode 30 of FIG. 3 then has a tip 36, in particular a tip 36 with three free ends 37, which in particular define a triangle in the tip. Although not readily discernible in FIG. 3, the free ends are advantageously located in the same plane transverse to the longitudinal axis of the electrode body 30. The free ends 37 are integrally connected to the electrode tip core 33 and then to the body 59 of the electrode and are made of a non-conductive material. The electrode tip 36 can thus be anchored in the myocardial tissue or in the trabecular network without introducing a current into the tissue. The current is made available by the windings 31 along the length of the head 30 and crosses the myocardium in its central region and not, as in the case of shock electrodes, in the anchoring region.

FIG. 4 shows a second embodiment of the electrode, in which the electrode 30 is composed of one or more metallic, electrically conductive windings 31 and of a blunt distal end 32, formed from the one or more last windings. Advantageously, the non-conductive end 32 of the electrode here extends past the winding region such that, when the electrode 30 is placed loosely into the right ventricle, this tip lies, by virtue of its advanced position or its weight, in the apex of the right ventricle but, like the electrode according to FIG. 3, does not feed directly into this apex of the right ventricle. The winding 31 in the electrode according to FIG. 4 has a tighter configuration such that, after emerging from the sheath of the electrode, the winding provides a continuous conductive surface, with no view of the central core. A uniform output of current from a continuous surface is thereby possible.

Figure 5:
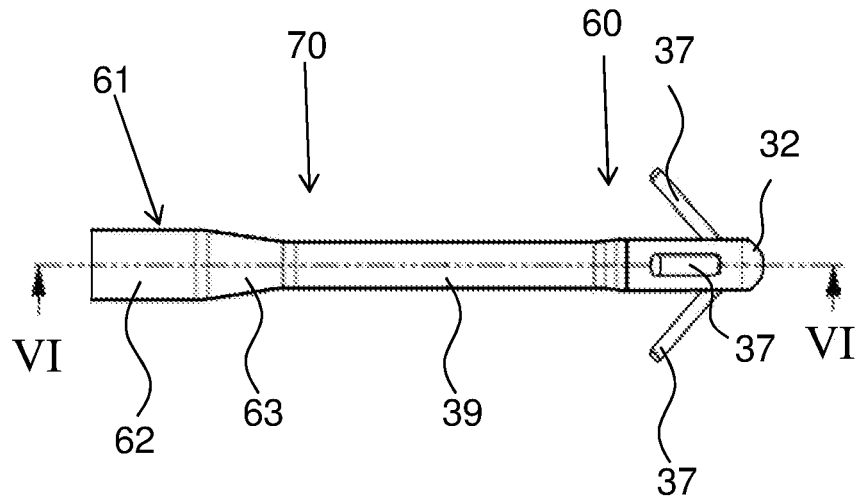
FIG. 5 shows a schematic representation of an anchor tip of a coil electrode according to an illustrative embodiment of the invention for use as a ventricular electrode as per FIG. 1 or FIG. 2.
Figure 6:
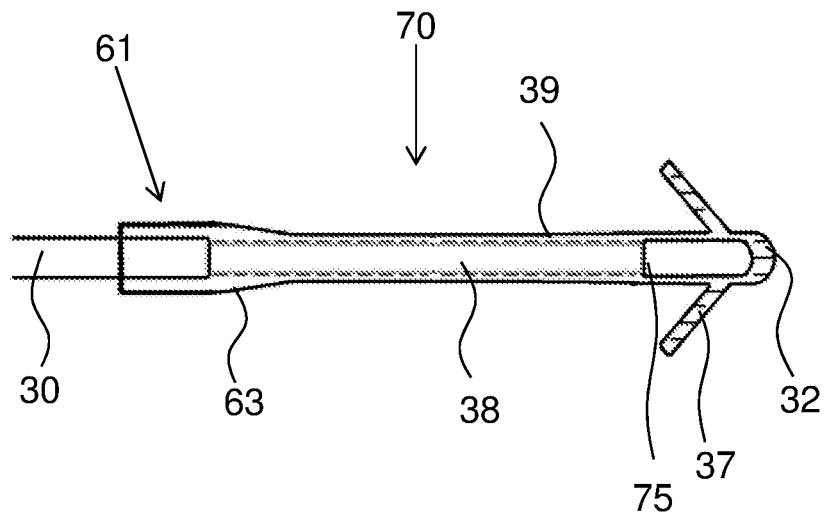
FIG. 6 shows a cross section through the anchor tip along the line VI-VI in FIG. 5, which anchor tip is placed onto a coil electrode tip.

FIG. 5 shows a schematic representation of an anchor tip 60 of a coil electrode according to an illustrative embodiment of the invention for use as a ventricular electrode according to FIG. 1 or FIG. 2, and FIG. 6 shows a cross section of the anchor tip 60 along the line VI-VI in FIG. 5, which anchor tip is placed onto a coil electrode tip.

The anchor region 60 comprises a tip with a blunt end 32 and with four anchoring tips 37 directed away from this blunt end 32. There follows a transition region 39, which can have a length of 1 to 3 centimeters. This transition region 39 then merges via a thickened part 63 into a flat-cylindrical connection region 62, which are rigidly connected as distal connector to the electrode. The anchor 70 is made entirely of electrically insulating material, in particular a plastic.

The anchor tips 37 are integrally connected to the hollow cylindrical anchor 70, as is seen in particular from the cross section in FIG. 6, wherein they are here bent back through 45 degrees relative to the longitudinal axis of the anchor, i.e. in the direction of the conductive region of the coil electrode. The connector 61 is fitted onto a metallic front portion of the electrode 30 reaching into the hollow cylindrical anchor 70. The anchor is fixed passively on the electrode. The end cap 75 in the front end region of the anchor 70, particularly in the region between the anchoring tips 37, stabilizes these and closes off the distal end of the electrode in order to avoid an inserted mandrel pushing through the anchor 70. The end cap 75 has a form-fit engagement on the inner face of the anchor 70 in order to strengthen the connection, advantageously obtained by adhesive, between electrode wire, end cap 75, distal fixture 61 and anchor 70, so as to achieve a high degree of operational strength under tensile loads. The end cap 75 itself has a hollow cylindrical shape and receives, in its interior, the engaged metallic tip of the electrode.

LIST OF REFERENCE SIGNS 10 heart
20 electrode assembly
30 ventricular coil electrode
31 electrically conductive winding
32 blunt end
33 electrode tip core
35 outlet
36 electrode tip
37 anchoring tip
38 core
39 transition region
40 coil electrode for coronary sinus
50 control circuit
51 single-conductor supply line 52 single-conductor supply line
55 arrow indicating current flow
58 single-conductor line
59 insulating sheath
60 anchor region
61 distal connector
62 flat-cylindrical connector
63 thickened part
70 anchor
75 end cap
140 surface electrode
141 edge of the surface electrode
152 single-conductor supply line
155 surface arrows

The invention claimed is:

1. An implantable direct-current electrode assembly comprising
   a first implantable electrode,
   a second implantable electrode, and
   a control circuit adapted to deliver a direct current,
   wherein the first implantable electrode and the second implantable electrode are electrically connected to the control circuit via a respective supply line,
   wherein the control circuit is designed to establish a potential difference between the first implantable electrode and the second implantable electrode, such that a direct current flows between the first implantable electrode and the second implantable electrode,
   wherein the first implantable electrode is a coil electrode configured to be positioned in the right ventricle between the tricuspid valve and the end of the right ventricle opposite the tricuspid valve and pulmonary valve,
   wherein the second implantable electrode is a surface electrode to be fastened at the exterior of the left ventricle, and
   wherein the direct current is a constant non-pulsing direct current.

2. The implantable direct-current electrode assembly as claimed in claim 1, wherein the electrical connection between the first implantable electrode and the control circuit, as well as between the second implantable electrode and the control circuit are provided as insulated, single-conductor lines.

3. The implantable direct-current electrode assembly as claimed in claim 1, wherein the first implantable electrode comprises an electrode core and one or more windings which are wound about the electrode core, wherein the electrode core is produced from electrically insulating material, wherein the supply line of the first implantable electrode comprises an insulating sheath and which electrode core is connected integrally to the insulating sheath of the supply line of the first implantable electrode.

4. The implantable direct-current electrode assembly as claimed in claim 3, wherein the electrode core of the first implantable coil electrode has a distal end which is blunt and extends past the end of the winding(s).

5. The implantable direct-current electrode assembly as claimed in claim 3, wherein the electrode core of the first implantable electrode has a distal end which is composed of a plurality of free ends protruding from one another and extending past the end of the winding(s).

6. The implantable direct-current electrode assembly as claimed in claim 5, wherein each free end of the plurality of free ends taper to a point.

7. The implantable direct-current electrode assembly as claimed in claim 5, wherein each free end of the plurality of free ends are hook-shaped.

8. A method for arranging an implantable direct-current electrode assembly comprising
   a first implantable electrode,
   a second implantable electrode, and
   a control circuit adapted to deliver a direct current,
   wherein the first implantable electrode and the second implantable electrode are electrically connected to the control circuit,
   wherein the control circuit is designed to establish a potential difference between the first implantable electrode and the second implantable electrode, such that a direct current flows between the first implantable electrode and the second implantable electrode,
   wherein the first implantable electrode is a coil electrode configured to be positioned in the right ventricle between the tricuspid valve and the end of the right ventricle opposite the tricuspid valve and pulmonary valve, and
   wherein the second implantable electrode is a surface electrode configured to be fastened at the exterior of the left ventricle,
   wherein the surface electrode is adapted to be applied to the side corresponding to the left ventricle, such that a triangular prism-shaped volume is defined between the first implantable electrode and the second implantable electrode, through which volume current flows when direct current is flowing between the first implantable electrode and the second implantable electrode, and
   wherein the direct current is a constant non-pulsing direct current.

\* \* \* \* \*